US011109876B2

(12) United States Patent
Kitamura et al.

(10) Patent No.: US 11,109,876 B2
(45) Date of Patent: Sep. 7, 2021

(54) SURGICAL TREATMENT INSTRUMENT

(71) Applicant: OLYMPUS CORPORATION, Hachioji (JP)

(72) Inventors: Ojiro Kitamura, Hachioji (JP); Yusuke Takei, Hino (JP); Yuki Kawaguchi, Koshu (JP)

(73) Assignee: OLYMPUS CORPORATION, Tokyo (JP)

( * ) Notice: Subject to any disclaimer, the term of this patent is extended or adjusted under 35 U.S.C. 154(b) by 91 days.

(21) Appl. No.: 16/382,379

(22) Filed: Apr. 12, 2019

(65) Prior Publication Data
US 2019/0231376 A1 Aug. 1, 2019

Related U.S. Application Data

(63) Continuation of application No. PCT/JP2016/080385, filed on Oct. 13, 2016.

(51) Int. Cl.
*A61B 17/29* (2006.01)
*A61B 18/08* (2006.01)
(Continued)

(52) U.S. Cl.
CPC .............. *A61B 17/29* (2013.01); *A61B 17/28* (2013.01); *A61B 17/2909* (2013.01);
(Continued)

(58) Field of Classification Search
CPC ..... A61B 17/29; A61B 17/28; A61B 17/2909; A61B 2017/003; A61B 2017/2927;
(Continued)

(56) References Cited

U.S. PATENT DOCUMENTS

2005/0006429 A1 1/2005 Wales et al.
2011/0213363 A1* 9/2011 Cunningham ..... A61B 18/1445
606/41
(Continued)

FOREIGN PATENT DOCUMENTS

| CN | 103281979 A | 9/2013 |
| JP | 2005-28150 A | 2/2005 |
| JP | 2013-540002 A | 10/2013 |

OTHER PUBLICATIONS

Nov. 29, 2016 International Search Report issued in International Patent Application PCT/JP2016/080385.
(Continued)

*Primary Examiner* — Melanie R Tyson
*Assistant Examiner* — Uyen N Vo
(74) *Attorney, Agent, or Firm* — Oliff PLC

(57) ABSTRACT

A surgical treatment instrument includes a holdable housing, a shaft, an end effector configured to perform a bending movement with respect to the shaft, a rotor configured to rotate about a rotation axis in response to an operation input performed through an operation member, and a transmission member configured to transmit a driving force for causing the end effector to perform the bending movement to the end effector. The operation member and the transmission member are configured to rotate together with the shaft and the end effector in response to the operation input, and the rotor is configured to not rotate together with the shaft and the end effector when the operation input is performed.

11 Claims, 8 Drawing Sheets

(51) Int. Cl.
  *A61B 18/12* (2006.01)
  *A61B 17/28* (2006.01)
  *A61B 17/00* (2006.01)

(52) U.S. Cl.
  CPC .......... *A61B 18/08* (2013.01); *A61B 18/1206* (2013.01); *A61B 2017/003* (2013.01); *A61B 2017/00327* (2013.01); *A61B 2017/293* (2013.01); *A61B 2017/2923* (2013.01); *A61B 2017/2927* (2013.01); *A61B 2017/2929* (2013.01); *A61B 2017/2937* (2013.01); *A61B 2017/2939* (2013.01); *A61B 2017/2947* (2013.01)

(58) Field of Classification Search
  CPC .... A61B 2017/2929; A61B 2017/2903; A61B 2017/2923; A61B 2017/293; A61B 2017/2936; A61B 2017/2937; A61B 2017/2938; A61B 2017/2939; A61B 2017/294; A61B 2017/2941; A61B 2017/2947; A61B 2017/00327; A61B 18/08; A61B 18/085; A61B 18/1445

See application file for complete search history.

(56) References Cited

U.S. PATENT DOCUMENTS

| | | |
|---|---|---|
| 2012/0074200 A1 | 3/2012 | Schmid et al. |
| 2012/0078243 A1* | 3/2012 | Worrell ............ A61B 17/07207 606/33 |
| 2015/0066022 A1* | 3/2015 | Shelton, IV ....... A61B 18/1445 606/41 |

OTHER PUBLICATIONS

Apr. 25, 2019 English Translation of IPRP and Written Opinion issued in International Application No. PCT/JP2016/080385.
Feb. 25, 2021 Office Action issued in Chinese Patent Application No. 201680090045.X.

\* cited by examiner

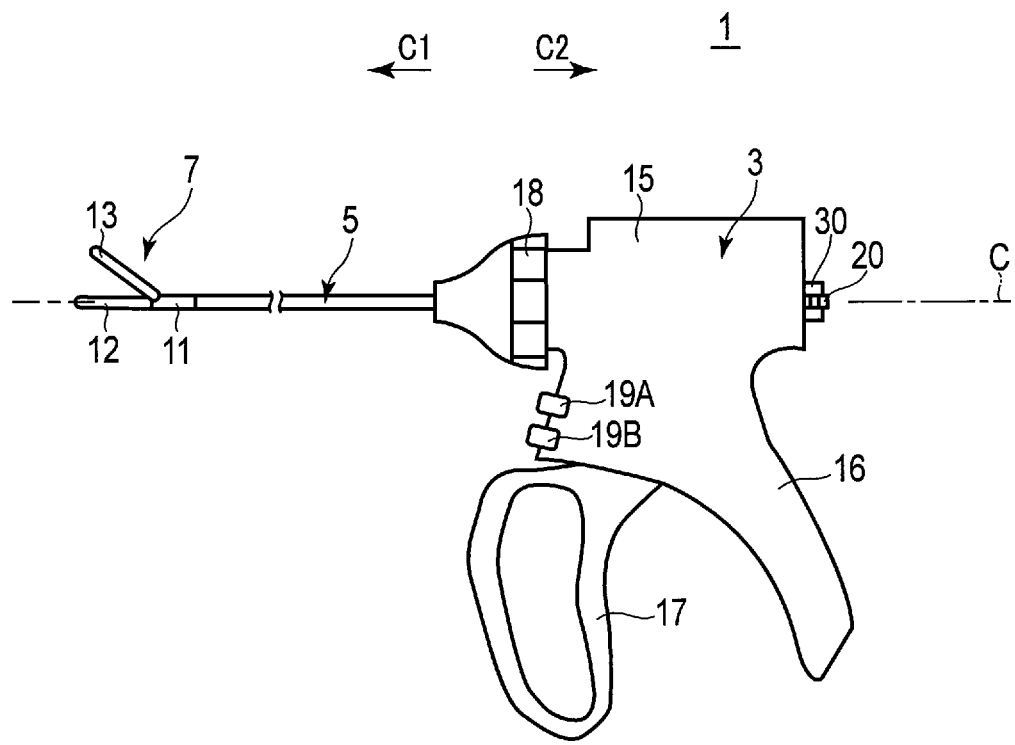
F I G. 1
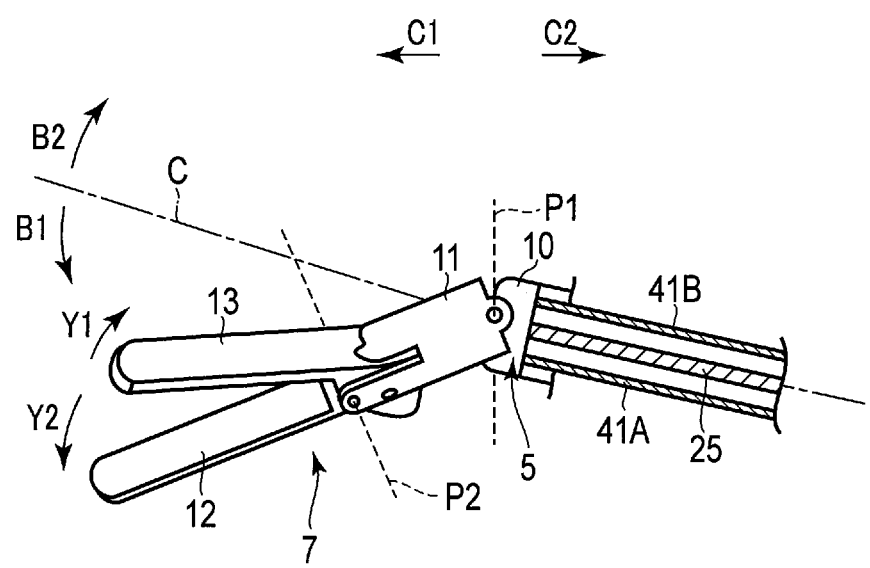
F I G. 2

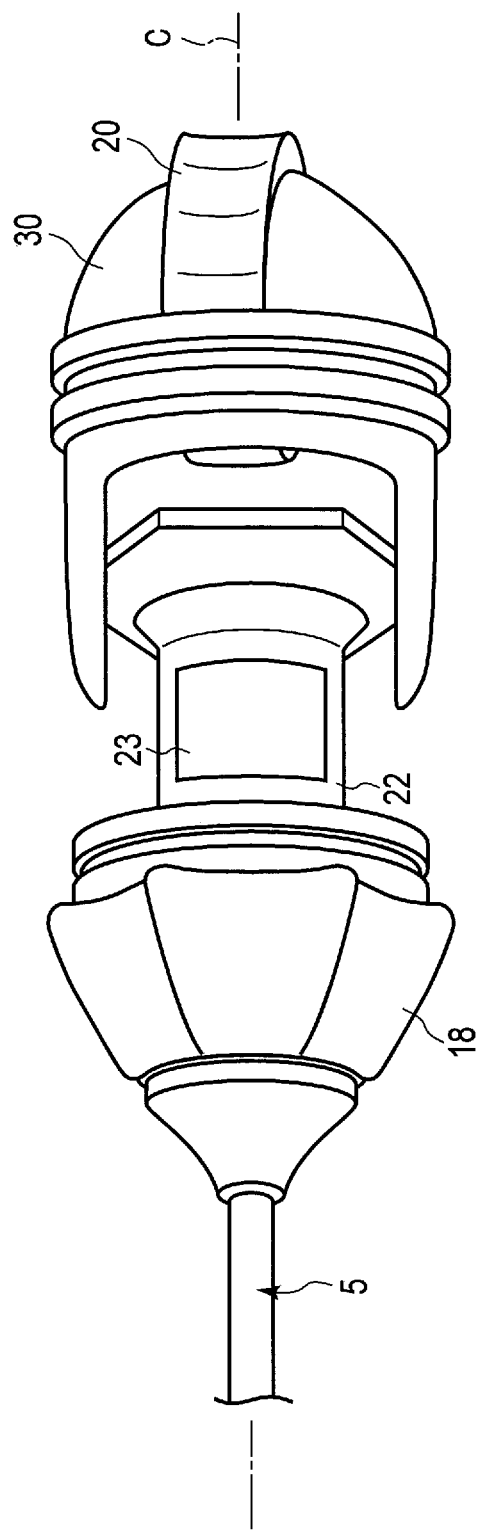
F I G. 3

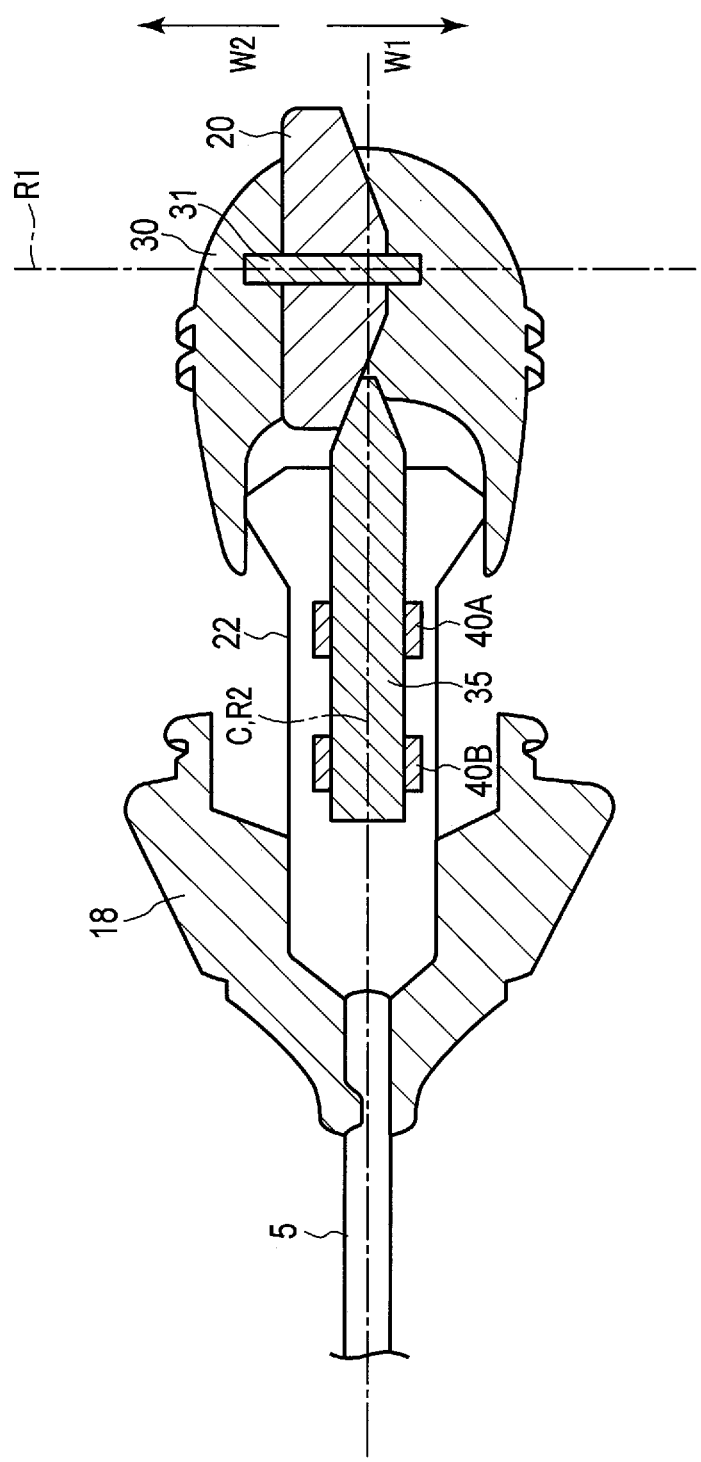
F I G. 4

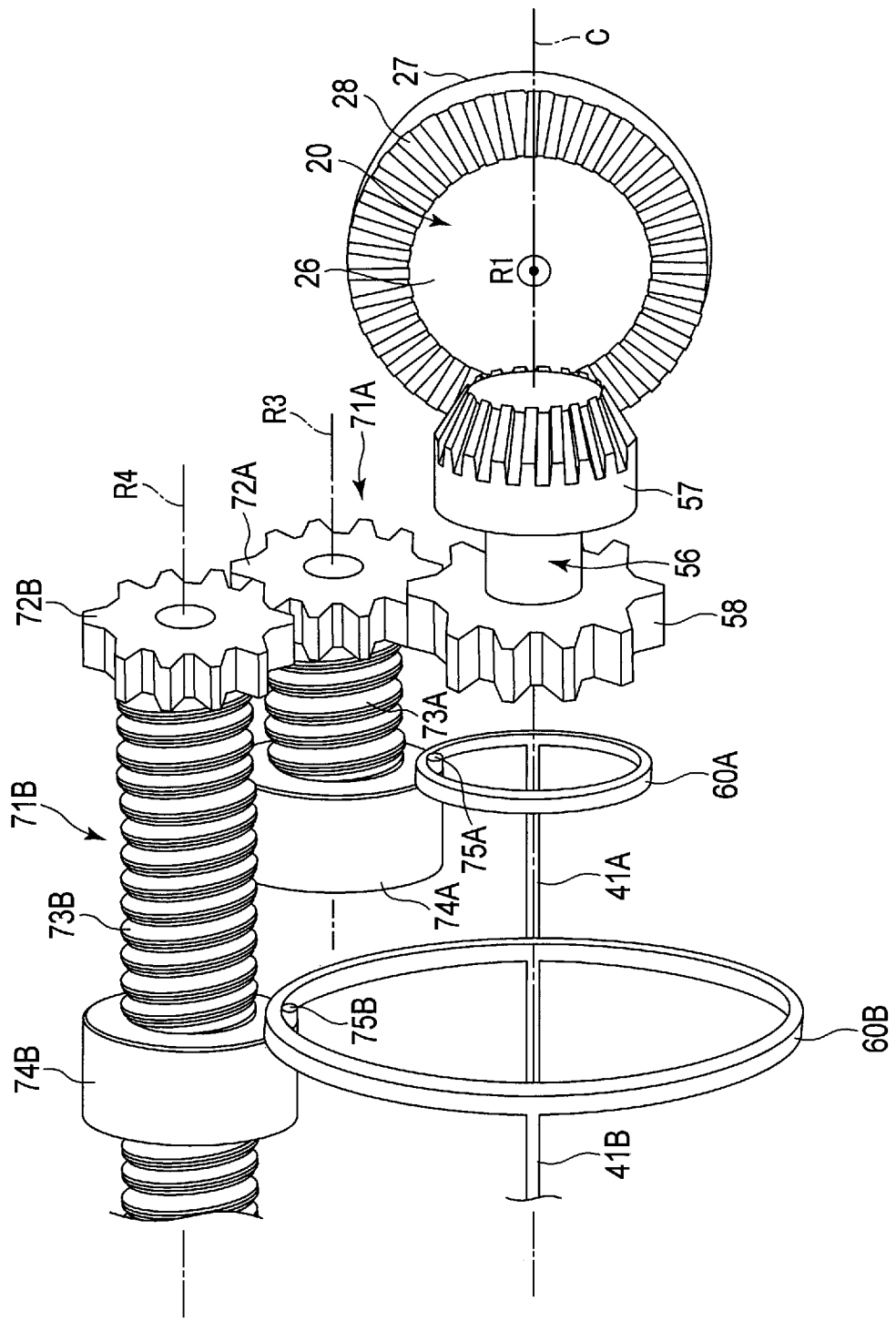
F I G. 10

SURGICAL TREATMENT INSTRUMENT

CROSS-REFERENCE TO RELATED APPLICATIONS

This is a Continuation Application of PCT Application No. PCT/JP2016/080385, filed Oct. 13, 2016, the entire contents of which are incorporated herein by reference.

BACKGROUND

1. Field of the Invention

The present exemplary embodiments relate to a surgical treatment instrument in which an end effector for treating a treatment target bends with respect to a shaft.

2. Description of the Related Art

In the related art, a surgical treatment instrument includes a shaft and an end effector that rotate about the longitudinal axis with respect to the housing in response to an operation input performed through a rotation operation knob (operation member) provided on the shaft. Also, in this surgical treatment instrument, the end effector is bendable with respect to the shaft, and the angle of the end effector with respect to the shaft (longitudinal axis) changes when the end effector bends. As the operation member through which the operation input for bending the end effector is performed, a bending operation dial is attached to the housing.

In the related art, the bending operation dial rotates independently of the rotation operation knob (shaft), so that when the rotation operation knob is rotated about the longitudinal axis, the bending operation dial does not rotate together with the shaft or the end effector. Hence, the relative relationship between the bending direction of the end effector and the operational direction (rotational direction) set by the bending operation dial changes as the angular position of the end effector about the longitudinal axis is changed in response to an operation input performed through the rotation operation knob.

SUMMARY

According to one aspect of the exemplary embodiments, a surgical treatment instrument includes an elongated member which defines a longitudinal axis and extends along the longitudinal axis from a proximal side to a distal side, a housing, a distal side of which is connected with the elongated member, an end effector attached to a distal side of the elongated member, and configured to bend with respect to the elongated member, a first operator configured to input an operation for rotating the elongated member and the end effector about the longitudinal axis with respect to the housing, a second operator attached to the housing, and configured to input an operation for causing the end effector to bend with respect to the elongated member, a rotor with a rotation axis, the rotor being provided inside the housing and configured to rotate about the rotation axis in response to the operation performed through the second operator, and a transmitter connected to the rotor and the end effector, and configured to transmit a driving force for causing the end effector to bend to the end effector when the rotor rotates about the rotation axis based on the operation performed through the second operator, wherein the second operator and the transmitter are configured to rotate about the longitudinal axis with respect to the housing together with the elongated member and the end effector in response to the operation performed through the first operator, and the rotor is configured to not rotate, together with the elongated member and the end effector, with respect to the housing about the longitudinal axis even when the operation is performed through the first operator.

Advantages of the exemplary embodiments will be set forth in the description which follows, and in part will be obvious from the description, or may be learned by practice of the exemplary embodiments. The advantages of the exemplary embodiments may be realized and obtained by means of the instrumentalities and combinations particularly pointed out hereinafter.

BRIEF DESCRIPTION OF THE DRAWING

The accompanying drawings, which are incorporated in and constitute a part of the specification, illustrate embodiments of the exemplary embodiments, and together with the general description given above and the detailed description of the embodiments given below, serve to explain the principles of the exemplary embodiments.

FIG. 1 is a schematic diagram of a surgical treatment instrument according to a first exemplary embodiment.

FIG. 2 is a schematic perspective view of a configuration of an end effector according to the first exemplary embodiment.

FIG. 3 is a schematic perspective view of an internal configuration of a housing according to the first exemplary embodiment.

FIG. 4 is a schematic sectional view of the internal configuration of the housing according to the first exemplary embodiment, which is observed at a cross section along the longitudinal axis.

FIG. 10 is a schematic perspective view of a configuration for transmitting a driving force for bending the end effector according to a third exemplary embodiment.

DETAILED DESCRIPTION

First Exemplary Embodiment

Figure 5:
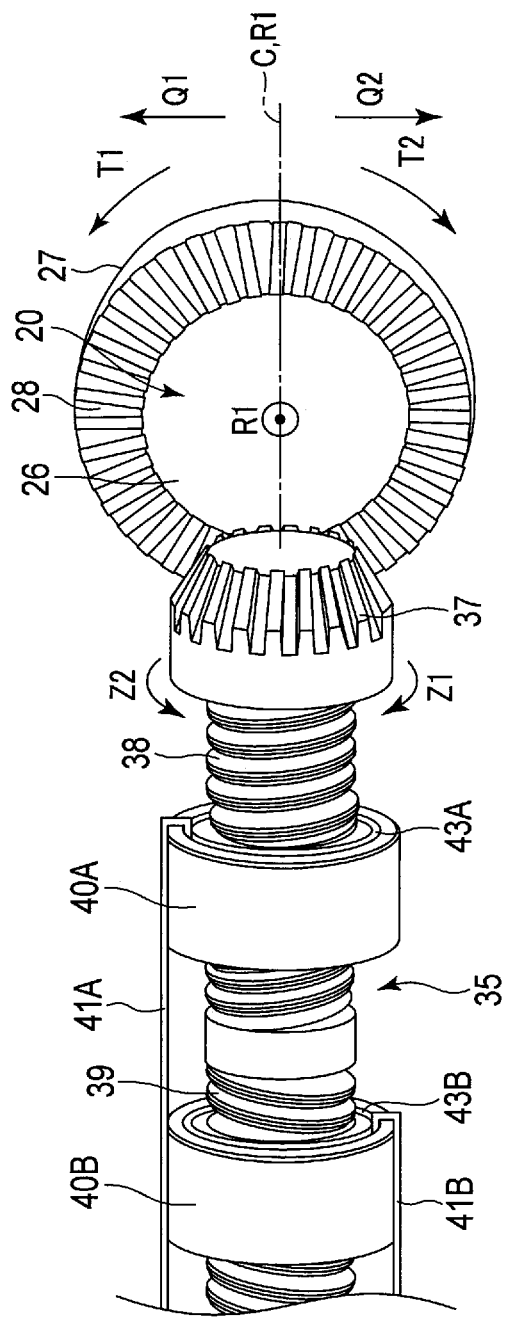
FIG. 5 is a schematic perspective view of a configuration for transmitting a driving force for bending the end effector according to the first exemplary embodiment.

A first exemplary embodiment will be described with reference to FIGS. 1 to 8.

FIG. 1 is a diagram illustrating a configuration of a surgical treatment instrument 1 according to the present embodiment. As illustrated in FIG. 1, the surgical treatment instrument 1 includes a holdable housing 3 and a tubular shaft (elongated member) 5 connected to the housing 3. The shaft 5 defines a longitudinal axis C. The direction along the longitudinal axis C is defined as a longitudinal direction. One side in the longitudinal direction is defined as the distal side (arrow C1 side in FIG. 1), and the opposite side from the distal side is defined as the proximal side (arrow C2 side in FIG. 1). The shaft 5 extends from the proximal side to the distal side along the longitudinal axis C, and is connected to the distal side of the housing 3.

The shaft 5 has a central axis substantially coaxial with the longitudinal axis C, and is installed to be rotatable about the longitudinal axis C with respect to the housing 3. A rotation operation knob 18 as a first operation member (a first operator) is attached to the proximal end of the shaft 5. The proximal end of the shaft 5 is inserted from the distal side into the rotation operation knob 18 and fixed to the rotation operation knob (rotation operation input unit) 18. The shaft 5 is extended from the rotation operation knob 18 toward the distal side. An end effector 7 for treating a treatment target is attached to the distal side of the shaft 5. When the rotation operation knob 18 is rotated about the longitudinal axis C with respect to the housing 3, the operation of rotating the end effector 7 about the longitudinal axis C is input through the rotation operation knob 18. When an operation input is performed through the rotation operation knob 18, a driving force (rotational driving force) is transmitted to the shaft 5, causing the rotation operation knob 18 and the shaft 5 to rotate together about the longitudinal axis C with respect to the housing 3.

FIG. 2 is a diagram illustrating a configuration of the end effector 7. As illustrated in FIG. 2, the end effector 7 includes an effector base 11 attached to the shaft 5, a first grasping piece 12 fixed to the effector base 11, and a second grasping piece 13 pivotably connected to the effector base 11. The effector base 11 is attached to the shaft 5 such that the effector base 11 is pivotable about a pivot axis (bending pivot axis) P1 with respect to the shaft 5. The pivot axis P1 extends along a direction intersecting with (substantially perpendicular to) the longitudinal direction of the shaft 5. As the end effector 7 including the effector base 11 pivots about the pivot axis P1 with respect to the shaft 5, the end effector 7 bends with respect to the shaft 5 in the directions indicated by arrow B1 and arrow B2 in FIG. 2.

The second grasping piece 13 can be pivoted about a pivot axis (opening/closing pivot axis) P2 with respect to the effector base 11. The pivot axis P2 extends along a direction intersecting with (substantially perpendicular to) the longitudinal direction and also intersecting with (substantially perpendicular to) the direction in which the pivot axis P1 extends. When the second grasping piece 13 pivots about the pivot axis P2, the first grasping piece 12 and the second grasping piece 13 are opened or closed with respect to each other in the end effector 7. More specifically, when the second grasping piece 13 pivots, the end effector 7 opens or closes in the directions indicated by arrow Y1 and arrow Y2 in FIG. 2. Both the first grasping piece 12 and the second grasping piece 13 may be attached to be pivotable with respect to the effector base 11 (e.g. about the pivot axis P2). In this case, the first grasping piece 12 and the second grasping piece 13 are opened or closed with respect to each other by pivoting the first grasping piece 12 and the second grasping piece 13 so as to open or close the end effector 7. In the present embodiment, a treatment target, such as a body tissue, is grasped between the first grasping piece 12 and the second grasping piece 13 in order to treat the treatment target.

As illustrated in FIG. 1, the housing 3 includes a housing main body 15, which is extended along the longitudinal axis C, and a grip (fixed handle) 16, which is extended from the housing main body 15 in a direction away from the longitudinal axis C. The shaft 5 is connected to the housing main body 15 from the distal side. A handle (movable handle) 17 is pivotably attached to the housing 3. The handle 17 is positioned on the side where the grip 16 is positioned with respect to the longitudinal axis C, and positioned on the distal side with respect to the grip 16 in the present embodiment. As the handle 17 pivots with respect to the housing 3, and opens or closes with respect to the grip 16, the operation for opening or closing the end effector 7 as described above is input through the handle 17, which is an opening/closing operation input unit. The handle 17 and the second grasping piece 13 are connected to each other via a movable member 25 extending in the shaft 5 along the longitudinal axis C. By opening or closing the handle 17, which is an opening/closing operation input unit, with respect to the grip 16, the movable member 25 moves along the longitudinal axis C with respect to the shaft 5 and the housing 3, and the second grasping piece 13 pivots about the pivot axis P2. As a result, the pair of grasping pieces 12 and 13 open or close.

Operation buttons 19A and 19B, which are energy operation input units, are attached to the housing 3. Performing an operation input through the operation button 19A, for example, supplies a high-frequency electric energy to the grasping pieces 12 and 13. Then, a high-frequency current is applied to the treatment target held between the grasping pieces 12 and 13 to thereby treat the treatment target. Performing an operation input through the operation button 19B supplies electric energy to, for example, a heating element (not illustrated) provided to the end effector 7. Then, the heat generated by the heating element is used to treat the treatment target. The energy supplied to the end effector 7 is not limited to the foregoing energy. Other types of energy used for treatment may be supplied to the end effector 7 by performing an operation input through the operation buttons 19A and 19B.

FIGS. 3 and 4 are diagrams illustrating the internal configuration of the housing 3 and the internal configuration of the rotation operation knob 18. FIG. 3 is a perspective view, and FIG. 4 illustrates a cross section that is substantially parallel to the longitudinal axis C. In the housing 3 (the housing main body 15), a tubular rotation base 22 as a base member (a base) is attached to the shaft 5 (the rotation operation knob 18) from the proximal side, as illustrated in FIGS. 3 and 4. An opening 23 that opens toward the outside of the rotation base 22 is provided on the outer peripheral surface of the rotation base 22. The rotation of the rotation base 22 about the longitudinal axis C with respect to the shaft 5 is restricted. For example, in a connecting portion between the rotation base 22 and the rotation operation knob 18, the cross-sectional shape of the outer peripheral surface of the rotation base 22 and the cross-sectional shape of the inner peripheral surface of the rotation operation knob 18 that are perpendicular to the longitudinal axis C are designed to be a polygonal shape, a D shape, or the like, so that the rotation of the rotation base 22 and the shaft 5 with respect to each other about the longitudinal axis C is restricted. The rotation base 22 is extended along the longitudinal axis C.

When the rotation operation knob 18 rotates about the longitudinal axis C in response to the operation input performed through the rotation operation knob 18, a driving force (rotational driving force) is transmitted to the rotation base 22 attached to the rotation operation knob 18, causing the rotation base 22 to rotate, with respect to the housing 3, about the longitudinal axis C together with the shaft 5 attached to the rotation operation knob 18. Since the shaft 5 is fixed to the rotation operation knob 18, the driving force (rotational driving force) is transmitted to the rotation base 22 through the rotation operation knob 18 when the shaft 5 is rotated.

According to the present embodiment, the movable member 25 is rotatable about the longitudinal axis C together with the shaft 5. Hence, in response to the operation input performed through the rotation operation knob 18, the end effector 7 rotates about the longitudinal axis C with respect to the housing 3 together with the shaft 5 and the movable member 25. As the end effector 7 rotates about the longitudinal axis C, the angular position of the end effector 7 about the longitudinal axis C with respect to the housing 3 changes.

As the end effector 7 rotates, the pivot axes P1 and P2 also rotate about the longitudinal axis C with respect to the housing 3, and the extending directions of the pivot axes P1 and P2 change accordingly. Thus, the bending directions of the bending movement of the end effector 7 (the side indicated by arrow B1 and the side indicated by arrow B2 in FIG. 2) and the opening/closing directions of the opening/closing movement thereof (the side indicated by arrow Y1 and the side indicated by arrow Y2 in FIG. 2) also change. However, the bending directions of the end effector 7 intersect with (are substantially perpendicular to) the longitudinal direction; and the opening/closing directions of the end effector 7 intersect with (are substantially perpendicular to) the longitudinal direction and also intersect with (are substantially perpendicular to) the bending directions of the bending movement, regardless of the angular position of the end effector 7 about the longitudinal axis C.

Inside the housing 3 (the housing main body 15), a rotation base 30 as a base member (a base) is attached to the rotation base 22 from the proximal side. The rotation base 30 is positioned closer to the proximal side than the rotation base 22. The rotation of the rotation base 30 about the longitudinal axis C with respect to the rotation base 22 is restricted. For example, in a connecting portion between the rotation bases 22 and 30, the cross-sectional shape of the outer peripheral surface of the rotation base 22 and the cross-sectional shape of the inner peripheral surface of the rotation base 30 that are perpendicular to the longitudinal axis C are designed to be a polygonal shape, a D shape, or the like, so that the rotation of the rotation bases 22 and 30 with respect to each other about the longitudinal axis C is restricted.

A bending operation dial 20 as a second operation member (a second operator) is attached to the housing 3. In the present embodiment, the bending operation dial (bending operation input unit) 20 is positioned on the proximal side apart from the rotation operation knob 18. An operation for bending the end effector 7 as described above is input through the bending operation dial 20. The bending operation dial 20 is attached to the housing 3 via the rotation base 30. The rotation base 30 and the bending operation dial 20 are rotatable about the longitudinal axis C with respect to the housing 3.

Figure 6:
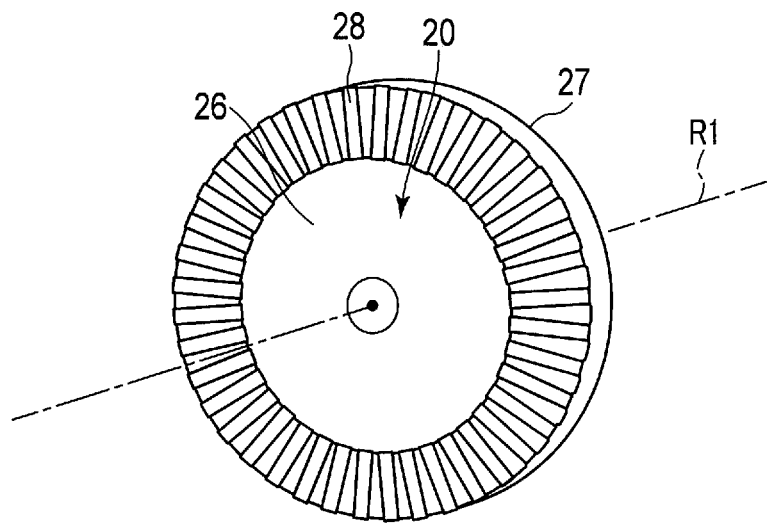
FIG. 6 is a schematic perspective view of a second operation member according to the first exemplary embodiment.

FIG. 5 is a perspective view illustrating a configuration for transmitting a driving force for bending the end effector 7. FIG. 6 is a view of the bending operation dial 20. As illustrated in FIGS. 4 to 6, the bending operation dial 20 is attached to the rotation base 30 via a support shaft 31. The bending operation dial 20 is rotatable about a central axis R1, which is the central axis of the support shaft 31, with respect to the rotation base 30. That is, the central axis R1 is the central axis (rotation axis) of the bending operation dial. The bending operation dial 20 is rotated about the central axis R1 so that an operation for bending the end effector 7 is input. At this time, the directions indicated by arrow Q1 and arrow Q2 in FIG. 5 are the operational directions set by the bending operation dial 20. The central axis R1 is extended along the direction intersecting with (substantially perpendicular to) the longitudinal axis C, and along the direction intersecting with (substantially perpendicular to) the operational directions set by the bending operation dial 20.

One side along the central axis R1 is defined as a first width direction side (arrow W1 side in FIG. 4) of the bending operation dial 20, and the opposite side from the first width direction side is defined as a second width direction side (arrow W2 side in FIG. 4). The bending operation dial 20 includes a first side surface 26 facing the first width direction side and a second side surface 27 facing the second width direction side. A gear section 28 is formed over the whole circumference of the first side surface 26 around the central axis R1. In the present embodiment, a part of the gear section 28 is exposed to the outside of the housing 3.

Figure 7:
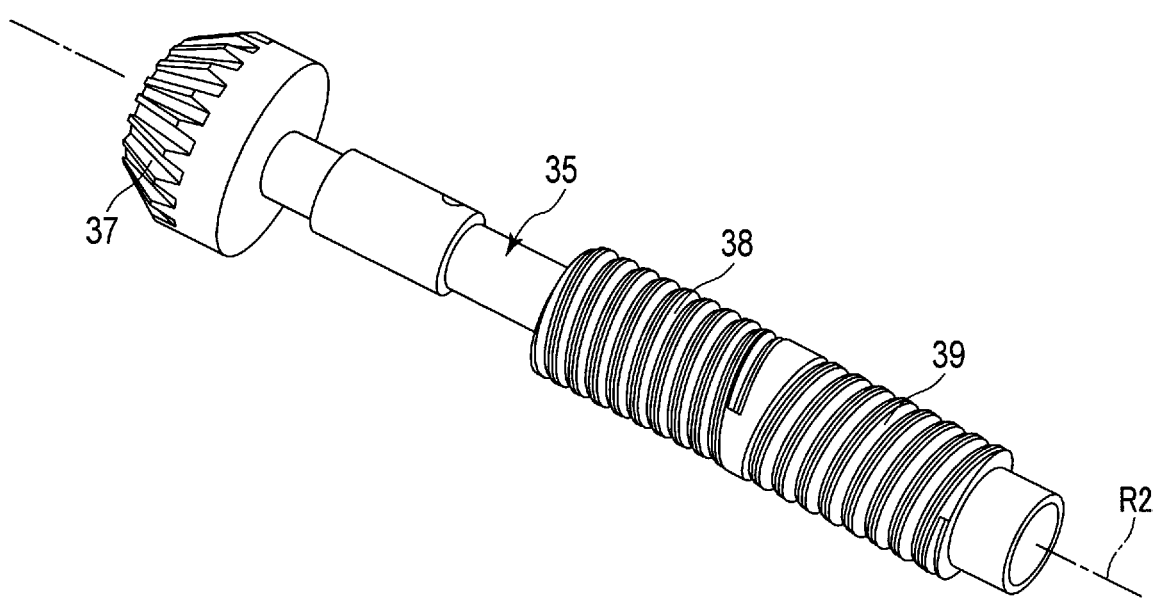
FIG. 7 is a schematic perspective view of a rotor according to the first exemplary embodiment.

A shaft 35 as a rotor is provided inside the rotation bases 22 and 30. FIG. 7 is a view of the shaft 35. As illustrated in FIGS. 5 and 7, the shaft 35 has a central axis (rotation axis) R2. In the present embodiment, the central axis R2 is substantially coincident (coaxial) with the longitudinal axis C. The shaft 35 extends along the central axis R2. The shaft 35 is attached to the housing main body 15 via a support member (not shown) extending through the opening 23, for example, in a state where the movement of the shaft 35 along the central axis R2 with respect to the housing 3 is restricted. The shaft 35 is rotatable about the central axis R2 with respect to the housing 3.

A gear section 37 is formed over the whole circumference of the proximal end of the shaft 35 around the central axis R2. The gear section 37 meshes with the gear section 28 of the bending operation dial 20. When the bending operation dial 20 rotates about the central axis R1 in response to an operation input performed through the bending operation dial 20, a driving force (rotational driving force) is transmitted to the gear section 37 through the gear section 28, causing the shaft 35 to rotate about the central axis R2. In the present embodiment, the bending operation dial 20 is rotatable with respect to the shaft 35 about the longitudinal axis C together with the rotation bases 22 and 30 while maintaining a state where the gear section 28 and the gear section 37 of the shaft 35 mesh with each other.

A bevel gear may be used for the gear section 28 and the gear section 37. Alternatively, a crown gear may be used for the gear section 28, and a spur gear is used for the gear section 37. Alternatively, a pin gear may be used for the gear section 28 and the gear section 37.

The shaft 35 includes a right-hand screw portion (first screw portion) 38 and a left-hand screw portion (second screw portion) 39. The right-hand screw portion (first screw) 38 includes a right-hand thread formed around the central axis R2. The left-hand screw portion (second screw) 39 includes a left-hand thread formed around the central axis R2. Therefore, the winding direction of the left-hand screw portion 39 is opposite to that of the right-hand screw portion 38, so that the left-hand screw portion 39 includes a thread reversed with respect to the right-hand screw portion 38.

Figure 8:
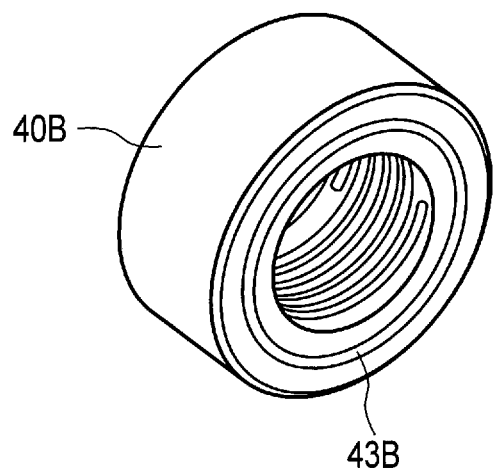
FIG. 8 is a schematic perspective view of a connecting member according to the first exemplary embodiment.

A nut 40A as a first connecting member (first connecter) is screwed to the right-hand screw portion 38. A nut 40B as a second connecting member (second connecter) is screwed to the left-hand screw portion 39. FIG. 8 is a view of the nut 40B. An internal thread of the right-hand thread is formed on the inner peripheral surface of the nut 40A. An internal thread of the left-hand thread is formed on the inner peripheral surface of the nut 40B. The nuts 40A and 40B are attached to the housing main body 15, for example, in a state where the rotation of the nuts 40A and 40B about the central axis R2 with respect to the housing 3 is restricted. The nuts 40A and 40B are movable along the central axis R2 with respect to the shaft 35, the rotation base 22, and the housing 3. The shaft 35 is rotatable about the central axis R2 with respect to the nuts 40A and 40B.

When the shaft 35 rotates about the central axis R2 in response to the operation input performed through the bending operation dial 20, the right-hand screw portion 38 rotates about the central axis R2 with respect to the nut 40A, and the left-hand screw portion 39 rotates about the central axis R2 with respect to the nut 40B. As a result, the nuts 40A and 40B move along the central axis R2 with respect to the shaft 35. That is, the shaft 35 as a rotor converts the rotational motion about the central axis R2 generated by the operation input performed through the bending operation dial 20 into a rectilinear motion of the nuts 40A and 40B along the central axis R2. The winding direction of the left-hand screw portion 39 is opposite to that of the right-hand screw portion 38. Therefore, the nuts 40A and 40B move in directions opposite to each other along the central axis R2.

A groove 43A is provided on the proximal face of the nut 40A. The groove 43A is provided around the central axis R2 and recessed from the proximal face of the nut 40A toward the distal side. The proximal end (one end) of a bending wire 41A as a transmission member (a transmitter) is fitted in the groove 43A. The bending wire (bending drive member) 41A is movable along the longitudinal axis C with respect to the rotation base 22. Also, the bending wire 41A is fitted in the groove 43A (nut 40A) in a state where the bending wire 41A is movable about the central axis R2 along the groove 43A. That is, the bending wire 41A as a transmission member is freely rotatable about the longitudinal axis C with respect to the nut 40A as a connecting member (connecter). The bending wire 41A is extended along the longitudinal axis C, and is extended through the inside of the rotation base 22 and the inside of the shaft 5 toward the distal side.

A groove 43B is provided on the proximal face of the nut 40B. The groove 43B is provided around the central axis R2 and recessed from the proximal face of the nut 40B toward the distal side. The proximal end (one end) of a bending wire 41B as a transmission member (a transmitter) is fitted in the groove 43B. The bending wire (bending drive member) 41B is movable along the longitudinal axis C with respect to the rotation base 22. Also, the bending wire 41B is fitted in the groove 43B (nut 40B) in a state where the bending wire 41B is movable about the central axis R2 along the groove 43B. That is, the bending wire 41B as a transmission member is freely rotatable about the longitudinal axis C with respect to the nut 40B as a connecting member (connecter). The bending wire 41B is extended along the longitudinal axis C, and is extended through the inside of the rotation base 22 and the inside of the shaft 5 toward the distal side.

As illustrated in FIG. 2, the distal ends (the other ends) of the bending wires 41A and 41B are connected to the effector base 11 of the end effector 7. When the shaft 35 rotates about the central axis R2 in response to the operation input performed through the bending operation dial 20, the nuts 40A and 40B move in directions opposite to each other with respect to the rotation base 22 along the central axis R2. Thus, the bending wires 41A and 41B as transmission members are driven, and the bending wires 41A and 41B move along the longitudinal axis C with respect to the shaft 5. As the bending wires 41A and 41B move, the end effector 7 bends with respect to the shaft 5, as described above. That is, the bending wires 41A and 41B as transmission members transmit the driving force for bending the end effector 7 to the end effector 7.

For example, if the bending operation dial 20 is rotated toward one side of the rotational direction (the side indicated by arrow T1 in FIG. 5) by the operation input for moving the bending operation dial 20 toward one side of the operational direction (the side indicated by arrow Q1 in FIG. 5), then the shaft 35 rotates toward one side of the rotational direction (the side indicated by arrow Z1 in FIG. 5). Thus, the nut 40A moves toward the distal side with respect to the shaft 35 and the rotation base 22, and the nut 40B moves toward the proximal side with respect to the shaft 35 and the rotation base 22. Accordingly, the nut 40A and the nut 40B move in directions opposite to each other. The bending wire 41A connected to the nut 40A moves toward the distal side (to be loosened), and the bending wire 41B connected to the nut 40B moves toward the proximal side (to be tightened), causing the end effector 7 to bend toward one side of the bending direction (the side indicated by arrow B2 in FIG. 2) with respect to the shaft 5 (the longitudinal axis C).

On the other hand, if the bending operation dial 20 is rotated toward the other side of the rotation direction (the side indicated by arrow T2 in FIG. 5) by the operation input for moving the bending operation dial 20 toward the other side of the operational direction (the side indicated by arrow Q2 in FIG. 5), then the shaft 35 rotates toward the other side of the rotational direction (the side indicated by arrow Z2 in FIG. 5). Thus, the nut 40A moves toward the proximal side with respect to the shaft 35 and the rotation base 22, and the nut 40B moves toward the distal side with respect to the shaft 35 and the rotation base 22. Accordingly, the nut 40A and the nut 40B move opposite to each other. The bending wire 41A moves toward the proximal side, and the bending wire 41B moves toward the distal side, causing the end effector 7 to bend toward the other side of the bending direction (the side indicated by arrow B1 in FIG. 2) with respect to the shaft 5 (the longitudinal axis C).

The bending wire 41B may be connected to the nut 40A, and the bending wire 41A may be connected to the nut 40B. In this case, when the operation input for moving the bending operation dial 20 toward one side of the operational direction (the side indicated by arrow Q1 in FIG. 5) is performed, for example, the bending wire 41B connected to the nut 40A moves toward the distal side (to be loosened), and the bending wire 41A connected to the nut 40B moves toward the proximal side (to be tightened), causing the end effector 7 to bend toward one side of the bending direction (the side indicated by arrow B1 in FIG. 2) with respect to the shaft 5 (the longitudinal axis C). Also, in response to the operation input for moving the bending operation dial 20 toward the other side of the operational direction (the side indicated by arrow Q2 in FIG. 5), the bending wire 41B connected to the nut 40A moves toward the proximal side (to be tightened), and the bending wire 41A connected to the nut 40B moves toward the distal side (to be loosened), causing the end effector 7 to bend toward the other side of the bending direction (the side indicated by arrow B2 in FIG. 2) with respect to the shaft 5 (the longitudinal axis C).

Inside the housing 3 (the housing main body 15), the rotation base 30 is connected to the rotation base 22 from the proximal side. The rotation of the rotation base 22 and the rotation base 30 about the longitudinal axis C with respect to each other is restricted. Therefore, the rotation bases 22 and 30, which connect the shaft 5 and the bending operation dial 20, are rotatable about the longitudinal axis C together with the shaft 5 and the bending operation dial 20.

The proximal end of each of the bending wires 41A and 41B is connected to one of the nuts 40A and 40B corresponding thereto, so as to be rotatable about the longitudinal axis C. The distal ends of the bending wires 41A and 41B are connected to the end effector 7. Therefore, the bending wires 41A and 41B, together with the shaft 5 and the end effector 7, are rotatable about the longitudinal axis C with respect to the shaft 35, the nuts 40A and 40B, and the housing 3.

With the foregoing configuration, the end effector 7, the shaft 5, and the rotation base 22 rotate about the longitudinal axis C in response to the operation input performed through the rotation operation knob (first operation member) 18, thereby transmitting a driving force (rotational driving force) to the rotation base 30 from the shaft 5 through the rotation base 22. This causes the rotation bases 22 and 30 to rotate, together with the end effector 7 and the shaft 5, about the longitudinal axis C with respect to the housing 3. At this time, the driving force (rotational driving force) is also transmitted from the end effector 7 to the bending wires 41A and 41B, which are connected to the end effector 7, so that the bending wires 41A and 41B rotate, together with the shaft 5, the end effector 7, and the rotation base 22, with respect to the housing 3 about the longitudinal axis C. The driving force (rotational driving force) is also transmitted from the rotation base 30 to the bending operation dial 20 and the support shaft 31, which are attached to the rotation base 30, so that the bending operation dial 20 and the support shaft 31 rotate, together with the rotation base 30, about the longitudinal axis C with respect to the housing 3. Namely, according to the present embodiment, when the shaft 5 rotates about the longitudinal axis C with respect to the housing 3 in response to the operation input performed through the rotation operation knob 18, which is the first operation member, the bending operation dial 20, which is the second operation member, the end effector 7, and the bending wires 41A and 41B also rotate, together with the shaft 5, about the longitudinal axis C with respect to the housing 3.

As described above, the bending operation dial 20 is rotatable, together with the rotation bases 22 and 30, about the longitudinal axis C with respect to the shaft 35 while maintaining a state where the gear section 28 and the gear section 37 of the shaft 35 mesh with each other. Therefore, a driving force (rotational driving force) for rotating the shaft 5 about the longitudinal axis C generated by the operation input performed through the rotation operation knob 18 is not transmitted from the rotation base 30 and the bending operation dial 20 to the shaft 35 and the nuts 40A and 40B. Each of the bending wires 41A and 41B is connected to one of the nuts 40A and 40B corresponding thereto, so as to be rotatable about the longitudinal axis C. Therefore, the driving force (rotational driving force) for rotating the shaft 5 about the longitudinal axis C is not transmitted from the end effector 7 and the bending wires 41A and 41B to the shaft 35 and the nuts 40A and 40B. Therefore, even when an operation input is performed through the rotation operation knob 18, the shaft 35 and the nuts 40A and 40B do not rotate, together with the shaft 5, the end effector 7, and the bending operation dial 20, with respect to the housing 3 about the longitudinal axis C.

The bending operation dial 20 rotates with respect to the shaft 35 about the longitudinal axis C in response to an operation input performed through the rotation operation knob 18. At this time, the gear section 28 rotates about the longitudinal axis C, and also moves on the outer peripheral surface of the gear section 37 along the central axis R2 (the longitudinal axis C) while maintaining the state of meshing with the gear section 37. Therefore, even if the angular position of the bending operation dial 20 about the longitudinal axis C relative to the shaft 35 changes, a driving force generated by the operation input performed through the bending operation dial 20 is transmitted to the shaft 35.

In the present embodiment, the bending wires 41A and 41B rotate with respect to the nuts 40A and 40B about the longitudinal axis C in response to the operation input performed through the rotation operation knob 18. At this time, the bending wires 41A and 41B move inside the grooves 43A and 43B around the central axis R2 (the longitudinal axis C) while being fitted in the grooves 43A and 43B. Therefore, even if the angular position of the bending wires 41A and 41B about the longitudinal axis C relative to the nuts 40A and 40B changes, a driving force generated by the operation input performed through the bending operation dial 20 is transmitted from the nuts 40A and 40B to the bending wires 41A and 41B.

As the bending operation dial 20 rotates about the longitudinal axis C, the central axis R1 also rotates about the longitudinal axis C with respect to the housing 3. At this time, the extending direction of the central axis R1 also changes. This in turn changes the rotational directions of the bending operation dial 20 (the side indicated by arrow T1 and the side indicated by arrow T2 in FIG. 5), thus changing the operational directions of the operation input performed through the bending operation dial 20 (the side indicated by arrow Q1 and the side indicated by arrow Q2 in FIG. 5). However, the operational direction set by the bending operation dial 20 intersects with (is substantially perpendicular to) the longitudinal axis C and the central axis R2, and intersects with (is substantially perpendicular to) the extending direction of the central axis R1, regardless of the angular positions of the rotation base 30 and the bending operation dial 20 about the longitudinal axis C.

As described above, according to the present embodiment, the shaft 5, the end effector 7, and the bending operation dial 20 rotate together about the longitudinal axis C in response to the operation input performed through the rotation operation knob 18. Hence, if the angular position of the end effector 7 about the longitudinal axis C changes due to the rotation of the end effector 7, the angular position of the bending operation dial 20 about the longitudinal axis C changes according to the change in the angular position of the end effector 7. Therefore, when the operation input is performed through the rotation operation knob 18, the operational directions set by the bending operation dial 20 (the side indicated by arrow Q1 and the side indicated by arrow Q2 in FIG. 5) change according to the changes in the bending directions of the end effector 7 (the side indicated by arrow B1 and the side indicated by arrow B2 in FIG. 2). For example, in one embodiment, the end effector 7 is rotated about the longitudinal axis C by the operation input performed through the rotation operation knob 18, from a state in which the bending direction of the end effector 7 and the operational direction set by the bending operation dial 20 are substantially parallel. At this time, the bending operation dial 20 also rotates about the longitudinal axis C together with the end effector 7, so that the state in which the bending direction of the end effector 7 and the operational direction set by the bending operation dial 20 are substantially parallel is maintained even when the angular position of the end effector 7 about the longitudinal axis C changes. Namely, according to the present embodiment, even when the operation input is performed through the rotation operation knob 18, the end effector 7 and the bending operation dial 20 rotate together about the longitudinal axis C without changing the relative relationship between the bending direction of the end effector 7 and the operational direction set by the bending operation dial 20. Also, even when the operation input is performed through the rotation operation knob 18, the driving force due to the operation input performed through the bending operation dial 20 is transmitted to the end effector 7 without changing the relative relationship between the bending direction of the end effector 7 and the operational direction set by the bending operation dial 20.

A description will now be given of the operation and effect of the surgical treatment instrument 1 according to the present embodiment. When performing a treatment by using the surgical treatment instrument 1, the end effector 7 is inserted into a body cavity, such as an abdominal cavity. Then, the end effector 7 is brought to a treatment target. At this time, the end effector 7 is rotated about the longitudinal axis C by the operation input performed through the rotation operation knob 18, or the end effector 7 is bent with respect to the shaft 5 by the operation input performed through the bending operation dial 20, so that the end effector 7 is placed at a position that allows the treatment target to be easily gripped. Then, the treatment target is positioned between the pair of the grasping pieces 12 and 13, and the end effector 7 is closed by the operation input performed through the handle 17. Thus, the treatment target is held between the grasping pieces 12 and 13. In this state, an operation input is performed through the operation button 19A or 19B to supply energy to the end effector 7, so that the treatment target is treated using the energy (treatment energy).

According to the present embodiment, the shaft 5, the end effector 7, and the bending operation dial 20 rotate together about the longitudinal axis C in response to the operation input performed through the rotation operation knob 18. Hence, even when the angular position of the end effector 7 about the longitudinal axis C with respect to the housing 3 changes, the relative angular position of the bending operation dial 20 about the longitudinal axis C with respect to the shaft 5 and the end effector 7 remains unchanged. Namely, even when an operation input is performed through the rotation operation knob 18, the end effector 7 and the bending operation dial 20 rotate together about the longitudinal axis C without changing the relative relationship between the bending directions of the end effector 7 (the side indicated by arrow B1 and the side indicated by arrow B2 in FIG. 2) and the operational directions set by the bending operation dial 20 (the side indicated by arrow Q1 and the side indicated by arrow Q2 in FIG. 5). This enables the operator to easily know the bending direction of the end effector 7 regardless of the angular position of the end effector 7 about the longitudinal axis C.

As described above, the present embodiment can provide the surgical treatment instrument 1 that ensures ease of operation for bending the end effector 7 with respect to the shaft 5 regardless of the angular position of the end effector 7 about the longitudinal axis C.

Modification Example of First Exemplary Embodiment

In one modification example of the first exemplary embodiment, the bending wire 41B is connected to the right-hand screw portion (first screw portion) 38 of the shaft 35, and the bending wire 41A is connected to the left-hand screw portion (second screw portion) 39 of the shaft 35. In this case, the movement of the nut (first connecting member) 40A and the nut (second connecting member) 40B along the central axis R2 with respect to the housing 3 is restricted.

The shaft 35 including the right-hand screw portion 38 and the left-hand screw portion 39 is movable along the central axis R2 with respect to the housing main body 15, the rotation bases 22 and 30, and the nuts 40A and 40B. On the shaft 35, the right-hand screw portion 38 and the left-hand screw portion 39 are connected to each other so as to be movable along the central axis R2. Also, in this modification example, the bending wires 41A and 41B are freely rotatable about the longitudinal axis C with respect to the shaft 35. In this modification example, in response to the operation input for moving the bending operation dial 20 toward one side of the operational direction, for example, the bending wire 41B connected to the right-hand screw portion 38 moves toward the distal side (to be loosened), and the bending wire 41A connected to the left-hand screw portion 39 moves toward the proximal side (to be tightened), causing the end effector 7 to bend toward one side of the bending direction with respect to the shaft 5 (the longitudinal axis C). Also, in response to the operation input for moving the bending operation dial 20 toward the other side of the operational direction, the bending wire 41B moves toward the proximal side, and the bending wire 41A moves toward the distal side, causing the end effector 7 to bend toward the other side of the bending direction with respect to the shaft 5 (the longitudinal axis C).

Second Exemplary Embodiment

Figure 9:
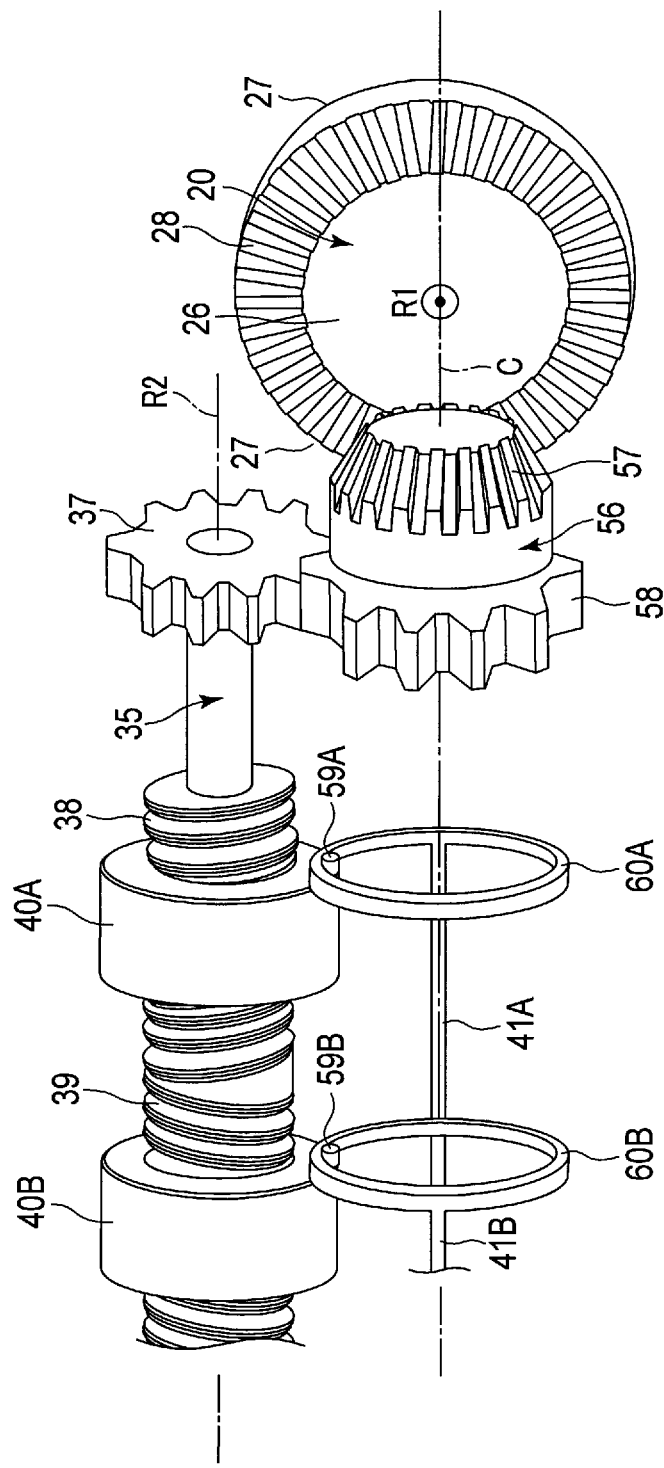
FIG. 9 is a schematic perspective view of a configuration for transmitting a driving force for bending the end effector according to a second exemplary embodiment.

Next, a second exemplary embodiment will be described with reference to FIG. 9. The same components as those described in the first exemplary embodiment will be denoted by the same reference symbols, and a description of those components will be omitted. FIG. 9 is a diagram illustrating a configuration for transmitting a driving force for bending the end effector 7 according to the present embodiment. In the present embodiment, the shaft 35, which is a rotor, is provided outside the rotation bases 22 and 30 in the housing main body 15, as illustrated in FIG. 9. Therefore, the shaft 35 extends along a direction substantially parallel to the longitudinal axis C at a position away from the longitudinal axis C. That is, the central axis (rotation axis) R2 of the shaft 35 is substantially parallel to the longitudinal axis C and is positioned away from the longitudinal axis C. The shaft 35 is attached to the housing main body 15, for example, in a state where the movement of the shaft 35 along the central axis R2 with respect to the housing 3 is restricted. The shaft 35 is rotatable about the central axis R2 with respect to the housing 3.

A connecting gear 56 is provided in the rotation bases 22 and 30. The connecting gear 56 extends along the longitudinal axis C. The shaft 35 is connected to the bending operation dial 20 via the connecting gear 56. The connecting gear 56 is attached to the housing main body 15, for example, via a support member (not shown) extending through the opening 23. The movement of the connecting gear 56 along the longitudinal axis C with respect to the rotation bases 22 and 30 and the housing 3 is restricted. Also, the connecting gear 56 is rotatable with respect to the rotation bases 22 and 30 and the housing 3 about the longitudinal axis C.

A first gear section 57 is provided on the proximal end of the connecting gear 56. The first gear section 57 meshes with the gear section 28 of the bending operation dial 20. In one exemplary embodiment, a bevel gear is used for the gear section 28 and the first gear section 57. Alternatively, a crown gear is used for the gear section 28, and a spur gear is used for the first gear section 57. Alternatively, a pin gear is used for the gear section 28 and the first gear section 57. In the present embodiment, the bending operation dial 20 is rotatable with respect to the connecting gear 56 about the longitudinal axis C together with the rotation bases 22 and 30 while maintaining a state where the gear section 28 and the first gear section 57 of the connecting gear 56 mesh with each other.

A second gear section 58 is provided on the distal end of the connecting gear 56. The second gear section 58 meshes with the gear section 37 of the shaft 35. For example, a spur gear is used for the second gear section 58 and the gear section 37.

When the bending operation dial 20 rotates about the central axis R1 in response to an operation input performed through the bending operation dial 20, a driving force (rotational driving force) is transmitted to the first gear section 57 through the gear section 28, causing the connecting gear 56 to rotate about the longitudinal axis C. When the connecting gear 56 rotates about the longitudinal axis C, a driving force (rotational driving force) is transmitted to the gear section 37 through the second gear section 58, causing the shaft 35 to rotate about the central axis R2.

The nut 40A as a first connecting member (first connecter) includes a protrusion 59A. The protrusion 59A protrudes from the proximal face of the nut 40A toward the proximal side. The nut 40B as a second connecting member (second connecter) includes a protrusion 59B. The protrusion 59B protrudes from the proximal face of the nut 40B toward the proximal side.

A ring portion 60A is provided on the proximal end of the bending wire 41A, which is a bending drive member (transmission member). The ring portion 60A has a ring shape with the longitudinal axis C as a central axis. A part of the ring portion 60A is exposed from the opening 23 to the outside of the rotation base 22. At the part of the ring portion 60A exposed to the outside of the rotation base 22, the protrusion 59A of the nut 40A is in contact with the inner peripheral surface of the ring portion 60A from the inside. As a result, the ring portion 60A is connected to the protrusion 59A of the nut 40A. The movement of the ring portion 60A along the longitudinal axis C with respect to the nut 40A is restricted. Therefore, when the nut 40A moves along the central axis R2 with respect to the shaft 35 in response to an operation input performed through the bending operation dial 20, a driving force is transmitted to the ring portion 60A via the protrusion 59A, causing the bending wire 41A to move along the longitudinal axis C with respect to the shaft 35 and the rotation base 22. Also, the bending wire 41A is rotatable about the longitudinal axis C with respect to the protrusion 59A and the nut 40A in a state where the ring portion 60A is connected to the protrusion 59A. That is, the bending wire 41A as a transmission member is freely rotatable about the longitudinal axis C with respect to the nut 40A as a connecting member (connecter).

A ring portion 60B is provided on the proximal end of the bending wire 41B, which is a bending drive member (transmission member). The ring portion 60B has a ring shape with the longitudinal axis C as a central axis. A part of the ring portion 60B is exposed from the opening 23 to the outside of the rotation base 22. At the part of the ring portion 60B exposed to the outside of the rotation base 22, the protrusion 59B of the nut 40B is in contact with the inner peripheral surface of the ring portion 60B from the inside. As a result, the ring portion 60B is connected to the protrusion 59B of the nut 40B. The movement of the ring portion 60B along the longitudinal axis C with respect to the nut 40B is restricted. Therefore, when the nut 40B moves along the central axis R2 with respect to the shaft 35 in response to an operation input performed through the bending operation dial 20, a driving force is transmitted to the ring portion 60B via the protrusion 59B, causing the bending wire 41B to move along the longitudinal axis C with respect to the shaft 35 and the rotation base 22. Also, the bending wire 41B is rotatable about the longitudinal axis C with respect to the protrusion 59B and the nut 40B in a state where the ring portion 60B is connected to the protrusion 59B. That is, the bending wire 41B as a transmission member is freely rotatable about the longitudinal axis C with respect to the nut 40B as a connecting member.

When the shaft 35 rotates about the central axis R2 in response to the operation input performed through the bending operation dial 20, the nut 40A and the nut 40B move in directions opposite to each other along the central axis R2. As the nut 40A and the nut 40B move in directions opposite to each other, the bending wires 41A and 41B are driven, so that the end effector 7 is bent.

In the present embodiment as well, the shaft 35 as a rotor converts the rotational motion about the central axis R2 generated by the operation input performed through the bending operation dial 20 into a rectilinear motion of the nuts 40A and 40B along the central axis R2.

The end effector 7, the shaft 5, the rotation bases 22 and 30, and the bending operation dial 20 together rotate with respect to the housing 3 about the longitudinal axis C in response to an operation input performed through the rotation operation knob 18. In the present embodiment, the bending operation dial 20 is rotatable, together with the rotation bases 22 and 30, about the longitudinal axis C with respect to the connecting gear 56 while maintaining a state where the gear section 28 and the first gear section 57 of the connecting gear 56 mesh with each other, as described above. Therefore, a driving force (rotational driving force) for rotating the shaft 5 about the longitudinal axis C generated by the operation input performed through the rotation operation knob 18 is not transmitted from the rotation base 30 and the bending operation dial 20 to the shaft 35 and the nuts 40A and 40B. In the present embodiment as well, each of the bending wires 41A and 41B is connected to one of the nuts 40A and 40B corresponding thereto, so as to be rotatable about the longitudinal axis C. Therefore, the driving force (rotational driving force) for rotating the shaft 5 about the longitudinal axis C is not transmitted from the end effector 7 and the bending wires 41A and 41B to the shaft 35 and the nuts 40A and 40B. Therefore, even when an operation input is performed through the rotation operation knob 18, the shaft 35 and the nuts 40A and 40B do not rotate, together with the end effector 7, the shaft 5, the rotation bases 22 and 30, and the bending operation dial 20, with respect to the housing 3 about the longitudinal axis C.

The bending operation dial 20 rotates with respect to the connecting gear 56 about the longitudinal axis C in response to an operation input performed through the rotation operation knob 18. At this time, the gear section 28 rotates about the longitudinal axis C, and also moves on the outer peripheral surface of the gear section 57 around the longitudinal axis C while maintaining the state of meshing with the gear section 57. Therefore, even if the angular position of the bending operation dial 20 about the longitudinal axis C relative to the connecting gear 56 changes, a driving force generated by the operation input performed through the bending operation dial 20 is transmitted to the connecting gear 56.

The bending wires 41A and 41B rotate with respect to the nuts 40A and 40B about the longitudinal axis C in response to the operation input performed through the rotation operation knob 18. At this time, the bending wires 41A and 41B rotate about the longitudinal axis C in a state where the ring portions 60A and 60B are connected to the protrusions 59A and 59B. Therefore, even if the angular position of the bending wires 41A and 41B about the longitudinal axis C relative to the nuts 40A and 40B changes, a driving force generated by the operation input performed through the bending operation dial 20 is transmitted to the bending wires 41A and 41B.

Third Exemplary Embodiment

Next, a third exemplary embodiment will be described with reference to FIG. 10. The same components as those described in the first exemplary embodiment and the second exemplary embodiment will be denoted by the same reference symbols, and a description of those components will be omitted. FIG. 10 is a diagram illustrating a configuration for transmitting a driving force for bending the end effector 7 according to the present embodiment. In the present embodiment, a first shaft 71A as a first rotor and a second shaft 71B as a second rotor are provided inside the housing main body 15, as illustrated in FIG. 10. The first shaft 71A and the second shaft 71B are provided outside the rotation bases 22 and 30 in the housing main body 15. The connecting gear 56 is provided inside the rotation bases 22 and 30, as in the second exemplary embodiment. In the present embodiment, as in the second exemplary embodiment, the bending operation dial 20 is rotatable, together with the rotation bases 22 and 30, about the longitudinal axis C with respect to the connecting gear 56 while maintaining a state where the gear section 28 and the first gear section 57 of the connecting gear 56 mesh with each other. The first shaft 71A is connected to the bending operation dial 20 via the connecting gear 56. The second shaft 71B is connected to the connecting gear 56 via the first shaft 71A. Therefore, the second shaft 71B is connected to the bending operation dial 20 via the first shaft 71A and the connecting gear 56.

The first shaft 71A extends along the central axis (first rotation axis) R3. The central axis R3 is substantially parallel to the longitudinal axis C and is positioned away from the longitudinal axis C. The first shaft 71A is attached to the housing main body 15, for example, in a state where the movement of the first shaft 71A along the central axis R3 with respect to the housing 3 is restricted. Also, the first shaft 71A is rotatable about the central axis R3 with respect to the housing 3.

A gear section 72A is provided on the proximal end of the first shaft 71A. The gear section 72A meshes with the second gear section 58 of the connecting gear 56. For example, a spur gear is used for the gear section 72A and the second gear section 58. When the connecting gear 56 rotates about the longitudinal axis C in response to the operation input performed through the bending operation dial 20, a driving force is transmitted to the gear section 72A through the second gear section 58, so that the first shaft 71A rotates about the central axis R3 with respect to the housing 3.

The second shaft 71B extends along the central axis (second rotation axis) R4. The central axis R4 is substantially parallel to the longitudinal axis C and is positioned away from the longitudinal axis C. The second shaft 71B is attached to the housing main body 15, for example, in a state where the movement of the second shaft 71B along the central axis R4 with respect to the housing 3 is restricted. The second shaft 71B is rotatable about the central axis R4 with respect to the housing 3.

A gear section 72B is provided on the proximal end of the second shaft 71B. The gear section 72B meshes with the gear section 72A of the first shaft 71A. For example, a spur gear is used for the gear section 72B. The gear section 72A of the first shaft 71A meshes with the second gear section 58 of the connecting gear 56 and the gear section 72B of the second shaft 71B at different positions around the central axis R3. When the first shaft 71A rotates about the central axis R3 in response to the operation input performed through the bending operation dial 20, a driving force is transmitted to the gear section 72B through the gear section 72A, so that the second shaft 71B rotates opposite to the first shaft 71A about the central axis R4 with respect to the housing 3.

The first shaft 71A includes a left-hand screw portion (first screw portion) 73A. The left-hand screw portion (first screw) 73A includes a left-hand thread formed around the central axis R3. A nut 74A as a first connecting member (first connecter) is screwed to the left-hand screw portion 73A. For example, the nut 74A is attached to the housing main body 15. The rotation of the nut 74A about the central axis R3 with respect to the housing 3 is restricted. The nut 74A is movable along the central axis R3 with respect to the housing 3. Therefore, when the first shaft 71A rotates about the central axis R3 with respect to the rotation base 22 in response to the operation input performed through the bending operation dial 20, the left-hand screw portion 73A rotates about the central axis R3 with respect to the nut 74A, and the nut 74A moves along the central axis R3 with respect to the shaft 71A and the rotation base 22.

The second shaft 71B includes a left-hand screw portion (second screw portion) 73B. The left-hand screw portion (second screw) 73B includes a left-hand thread formed around the central axis R4. Therefore, the winding direction of the left-hand screw portion 73B is the same as that of the left-hand screw portion 73A. A nut 74B as a second connecting member (second connecter) is screwed to the left-hand screw portion 73B. For example, the nut 74B is attached to the housing main body 15. The rotation of the nut 74B about the central axis R4 with respect to the housing 3 is restricted. The nut 74B is movable along the central axis R4 with respect to the housing 3. Therefore, as the second shaft 71B rotates about the central axis R4 with respect to the rotation base 22, the left-hand screw portion 73B rotates about the central axis R4 with respect to the nut 74B, and the nut 74B moves along the central axis R4 with respect to the shaft 71B and the rotation base 22.

The nut 74A includes a protrusion 75A. The protrusion 75A protrudes from the proximal face of the nut 74A toward the proximal side. The nut 74B includes a protrusion 75B. The protrusion 75B protrudes from the proximal face of the nut 74B toward the proximal side.

As in the second exemplary embodiment, a ring portion 60A is provided on the proximal end of the bending wire 41A, which is a bending drive member (transmission member). The ring portion 60A has a ring shape with the longitudinal axis C as a central axis. A part of the ring portion 60A is exposed from the opening 23 to the outside of the rotation base 22. At the part of the ring portion 60A exposed to the outside of the rotation base 22, the protrusion 75A of the nut 74A is in contact with the inner peripheral surface of the ring portion 60A from the inside. As a result, the ring portion 60A is connected to the protrusion 75A of the nut 74A. The movement of the ring portion 60A along the longitudinal axis C with respect to the nut 74A is restricted. Therefore, when the nut 74A moves along the central axis R2 with respect to the shaft 71A in response to an operation input performed through the bending operation dial 20, a driving force is transmitted to the ring portion 60A via the protrusion 75A, causing the bending wire 41A to move along the longitudinal axis C with respect to the shaft 71A and the rotation base 22. Also, the bending wire 41A is rotatable about the longitudinal axis C with respect to the protrusion 75A and the nut 74A in a state where the ring portion 60A is connected to the protrusion 75A. That is, the bending wire 41A as a transmission member is freely rotatable about the longitudinal axis C with respect to the nut 74A as a connecting member (connecter).

A ring portion 60B is provided on the proximal end of the bending wire 41B, which is a bending drive member (transmission member). The ring portion 60B has a ring shape with the longitudinal axis C as a central axis. A part of the ring portion 60B is exposed from the opening 23 to the outside of the rotation base 22. At the part of the ring portion 60B exposed to the outside of the rotation base 22, the protrusion 75B of the nut 74B is in contact with the inner peripheral surface of the ring portion 60B from the inside. As a result, the ring portion 60B is connected to the protrusion 75B of the nut 74B. The movement of the ring portion 60B along the longitudinal axis C with respect to the nut 74B is restricted. Therefore, when the nut 74B moves along the central axis R2 with respect to the shaft 71B in response to an operation input performed through the bending operation dial 20, a driving force is transmitted to the ring portion 60B via the protrusion 75B, causing the bending wire 41B to move along the longitudinal axis C with respect to the shaft 71B and the rotation base 22. Also, the bending wire 41B is rotatable about the longitudinal axis C with respect to the protrusion 75B and the nut 74B in a state where the ring portion 60B is connected to the protrusion 75B. That is, the bending wire 41B as a transmission member is freely rotatable about the longitudinal axis C with respect to the nut 40B as a connecting member (connecter).

In the present embodiment as well, the shaft 71A as a rotor converts the rotational motion about the central axis R3 generated by the operation input performed through the bending operation dial 20 into a rectilinear motion of the nut 74A along the central axis R3. Also, the shaft 71B as a rotor converts the rotational motion about the central axis R4 generated by the operation input performed through the bending operation dial 20 into a rectilinear motion of the nut 74B along the central axis R4.

In the present embodiment, when the operation input is performed through the bending operation dial 20, the shaft 71A rotates about the central axis R3 with respect to the housing 3, and the shaft 71B rotates opposite to the shaft 71A about the central axis R4 with respect to the housing 3. Accordingly, the left-hand screw portion 73A and the left-hand screw portion 73B rotate in directions opposite to each other. Therefore, the nut 74A and the nut 74B move toward the sides opposite to each other in a direction substantially parallel to the longitudinal axis C. As the nut 74A and the nut 74B move in directions opposite to each other, the bending wires 41A and 41B are driven, so that the end effector 7 is bent.

The end effector 7, the shaft 5, the rotation bases 22 and 30, and the bending operation dial 20 together rotate with respect to the housing 3 about the longitudinal axis C in response to the operation input performed through the rotation operation knob 18. In the present embodiment as well, the bending operation dial 20 is rotatable with respect to the connecting gear 56 about the longitudinal axis C together with the rotation bases 22 and 30 while maintaining a state where the gear section 28 and the first gear section 57 of the connecting gear 56 mesh with each other, as described above. Therefore, a driving force (rotational driving force) for rotating the shaft 5 about the longitudinal axis C generated by the operation input performed through the rotation operation knob 18 is not transmitted from the rotation base 30 and the bending operation dial 20 to the shafts 71A and 71B and the nuts 74A and 74B. In the present embodiment, each of the bending wires 41A and 41B is connected to one of the nuts 74A and 74B corresponding thereto, so as to be rotatable about the longitudinal axis C. Therefore, the driving force (rotational driving force) for rotating the shaft 5 about the longitudinal axis C is not transmitted from the end effector 7 and the bending wires 41A and 41B to the shafts 71A and 71B and the nuts 74A and 74B. Therefore, even when an operation input is performed through the rotation operation knob 18, the shafts 71A and 71B and the nuts 74A and 74B do not rotate, together with the end effector 7, the shaft 5, the rotation bases 22 and 30, and the bending operation dial 20, with respect to the housing 3 about the longitudinal axis C.

Modification Example of Third Exemplary Embodiment

In a modification example of the third exemplary embodiment, the bending wire 41B is connected to the left-hand screw portion 73A of the first shaft (first rotor) 71A, and the bending wire 41A is connected to the left-hand screw portion 73B of the second shaft (second rotor) 71B. In this case, the movement of the nut (first connecting member) 74A along the central axis R3 with respect to the housing 3 is restricted, and the movement of the nut (second connecting member) 74B along the central axis R4 with respect to the housing 3 is restricted. The shaft 71A is movable along the central axis R3 with respect to the housing 3 and the nut 74A, and the shaft 71B is movable along the central axis R4 with respect to the housing 3 and the nut 74B. The bending wire 41A is freely rotatable about the longitudinal axis C with respect to the first shaft 71A, and the bending wire 41B is freely rotatable about the longitudinal axis C with respect to the second shaft 71B. In this modification example, in response to the operation input for moving the bending operation dial 20 toward one side of the operational direction, for example, the bending wire 41B connected to the shaft 71A moves toward the distal side (to be loosened), and the bending wire 41A connected to the shaft 71B moves toward the proximal side (to be tightened), causing the end effector 7 to bend toward one side of the bending direction (the side indicated by arrow B1 in FIG. 2) with respect to the shaft 5 (the longitudinal axis C). Also, in response to the operation input for moving the bending operation dial 20 toward the other side of the operational direction, the bending wire 41B moves toward the proximal side, and the bending wire 41A moves toward the distal side, causing the end effector 7 to bend toward the other side of the bending direction (the side indicated by arrow B2 in FIG. 2) with respect to the shaft 5 (the longitudinal axis C).

Additional advantages and modifications will readily occur to those skilled in the art. Therefore, the exemplary embodiments in their broader aspects are not limited to the specific details and representative exemplary embodiments shown and described herein. Accordingly, various modifications may be made without departing from the spirit or scope of the general inventive concept as defined by the appended claims and their equivalents.

What is claimed is:

1. A surgical treatment instrument comprising:
an elongated member having a longitudinal axis, the elongated member extending along the longitudinal axis from a proximal side to a distal side of the elongated member;
a housing connected to the elongated member at a distal side of the housing;
an end effector attached to the distal side of the elongated member, the end effector being configured to bend relative to the elongated member;
a first operator configured to rotate the elongated member and the end effector about the longitudinal axis with respect to the housing;
a second operator attached to the housing, the second operator being configured to bend the end effector relative to the elongated member;
a rotor having a rotation axis parallel to the longitudinal axis of the elongated member, the rotor being provided inside the housing and configured to rotate about the rotation axis of the rotor in response to an operation performed by the second operator to bend the end effector; and
a transmitter connected to the rotor and the end effector, the transmitter being configured to transmit a driving force to the end effector causing the end effector to bend, in response to the rotor rotating about the rotation axis of the rotor based on the operation performed by the second operator to bend the end effector,
wherein in response to performing the operation by the first operator to rotate the elongated member and the end effector:
the second operator and the transmitter are configured to rotate about the longitudinal axis with respect to the housing together with the elongated member and the end effector, and
the rotor is configured to not rotate, together with the elongated member and the end effector, with respect to the housing about the longitudinal axis.

2. The surgical treatment instrument according to claim 1, wherein the rotor is configured to rotate based on the operation performed by the second operator to convert a rotational motion into a rectilinear motion.

3. The surgical treatment instrument according to claim 1, wherein the rotation axis of the rotor is coaxial with the longitudinal axis of the elongated member.

4. The surgical treatment instrument according to claim 1, further comprising:
a connecter attached to the rotor, the connecter being connected to the transmitter, and the connecter being configured to move along the rotation axis with respect to the housing and the rotor in response to the rotor rotating about the rotation axis with respect to the housing, wherein:
a movement of the rotor along the rotation axis with respect to the housing is restricted, and
the transmitter is freely rotatable about the longitudinal axis with respect to the connecter, and the transmitter is configured to move along the longitudinal axis in response to the connecter moving along the rotation axis with respect to the housing and the rotor.

5. The surgical treatment instrument according to claim 4, wherein:
the rotor includes:
a first screw, and
a second screw having a winding direction that is opposite to a winding direction of the first screw;
the connecter includes:
a first connecter connected to the transmitter and attached to the first screw, and
a second connecter connected to the transmitter and attached to the second screw; and
the first connecter and the second connecter are configured to move in opposite directions along the rotation axis in response to the rotor rotating about the rotation axis with respect to the housing.

6. The surgical treatment instrument according to claim 4, wherein:
the rotor includes:
a first rotor having a first rotation axis, the first rotor including a first screw and being configured to rotate about the first rotation axis in response to the operation performed by the second operator, and
a second rotor having a second rotation axis, the second rotor including a second screw and being configured to rotate about the second rotation axis in response to the operation performed by the second operator; and
the connecter includes:
a first connecter connected to the transmitter, the first connector being attached to the first screw, the first connector being configured to move along the first rotation axis with respect to the housing and the first rotor in response to the first rotor rotating about the first rotation axis with respect to the housing, and
a second connecter connected to the transmitter, the second connector being attached to the second screw, the second connector being configured to move along the second rotation axis with respect to the housing and the second rotor in response to the second rotor rotating about the second rotation axis with respect to the housing.

7. The surgical treatment instrument according to claim 1, further comprising a connecter attached to the rotor and attached to the housing in a state where a movement of the connecter along the rotation axis with respect to the housing is restricted, wherein:
the rotor is connected with the transmitter, and the rotor is configured to rotate about the rotation axis with respect to the housing to move along the rotation axis with respect to the housing and the connecter; and
the transmitter is freely rotatable about the longitudinal axis with respect to the connecter, and the transmitter is configured to move along the longitudinal axis in response to the rotor moving along the rotation axis with respect to the housing and the connecter.

8. The surgical treatment instrument according to claim 7, wherein:
the rotor includes:
a first screw connected to the transmitter, and
a second screw connected to the transmitter, the second screw having a winding direction that is opposite to a winding direction of the first screw;
the connecter includes:
a first connecter attached to the first screw, and
a second connecter attached to the second screw; and
the first screw and the second screw are configured to move in opposite directions along the rotation axis in response to the rotor rotating about the rotation axis with respect to the housing.

9. The surgical treatment instrument according to claim 7, wherein:
the rotor includes:
a first rotor having a first rotation axis, the first rotor being configured to rotate about the first rotation axis in response to the operation performed by the second operator;
a second rotor having a second rotation axis, the second rotor being configured to rotate about the second rotation axis in response to the operation performed by the second operator;
a first screw provided to the first rotor and connected with the transmitter; and
a second screw provided to the second rotor and connected with the transmitter;
the connecter includes:
a first connecter attached to the first screw, and
a second connecter attached to the second screw;
the first rotor is configured to rotate about the first rotation axis with respect to the housing, and the first rotor is configured to move along the first rotation axis with respect to the housing and the first connecter; and
the second rotor is configured to rotate about the second rotation axis with respect to the housing, and the second rotor is configured to move along the second rotation axis with respect to the housing and the second connecter.

10. The surgical treatment instrument according to claim 1, wherein at all angular positions of the second operator about the longitudinal axis, an operational direction of the operation performed by the second operator is parallel to a bending direction of the bending of the end effector with respect to the elongated member.

11. The surgical treatment instrument according to claim 10, wherein the second operator has a central axis, which is parallel to the bending direction of the end effector and a direction intersecting with the longitudinal axis, and the second operator is configured to rotate about the central axis with respect to the housing in response to the operation performed by the second operator.

* * * * *